US009008271B2

(12) United States Patent
Burshtein et al.

(10) Patent No.: US 9,008,271 B2
(45) Date of Patent: Apr. 14, 2015

(54) SYSTEM FOR X-RAY IRRADIATION OF TARGET VOLUME

(75) Inventors: Zeev Burshtein, Nes-Ziona (IL); Aharon Bar-David, Nesher (IL); Zeev Harel, Kfar Saba (IL)

(73) Assignee: Convergent R.N.R. Ltd, Tirat Hakarmel (IL)

( * ) Notice: Subject to any disclaimer, the term of this patent is extended or adjusted under 35 U.S.C. 154(b) by 0 days.

(21) Appl. No.: 13/817,562

(22) PCT Filed: Aug. 18, 2011

(86) PCT No.: PCT/IL2011/000675
§ 371 (c)(1),
(2), (4) Date: Mar. 15, 2013

(87) PCT Pub. No.: WO2012/023141
PCT Pub. Date: Feb. 23, 2012

(65) Prior Publication Data
US 2013/0170625 A1    Jul. 4, 2013

Related U.S. Application Data

(60) Provisional application No. 61/375,056, filed on Aug. 19, 2010.

(51) Int. Cl.
G21K 1/06 (2006.01)
A61N 5/10 (2006.01)
G21K 5/04 (2006.01)

(52) U.S. Cl.
CPC .............. *G21K 1/06* (2013.01); *A61N 5/1042* (2013.01); *A61N 5/1084* (2013.01); *A61N 2005/1091* (2013.01); *A61N 2005/1095* (2013.01); *G21K 5/04* (2013.01)

(58) Field of Classification Search
CPC ... G21K 1/06; G21K 1/062; G21K 2201/064; G21K 2201/067
USPC .............................. 378/84, 85, 145, 147, 148
See application file for complete search history.

(56) References Cited

U.S. PATENT DOCUMENTS

| 2,688,094 | A | 8/1954 | Dumond |
| 5,004,319 | A | 4/1991 | Smither |
| 5,332,908 | A | 7/1994 | Weidlich |
| 6,389,100 | B1 | 5/2002 | Verman et al. |
| 6,624,431 | B1 | 9/2003 | Foster et al. |
| 2002/0080916 | A1 | 6/2002 | Jiang et al. |
| 2003/0142786 | A1* | 7/2003 | Houge ........................... 378/84 |
| 2004/0170250 | A1* | 9/2004 | Verman et al. .................. 378/84 |
| 2007/0030956 | A1* | 2/2007 | Hornig .......................... 378/119 |
| 2010/0149505 | A1 | 6/2010 | Sewell et al. |

OTHER PUBLICATIONS

Podorov et al., An optimized two crystal arrangement for X-ray optics, Optics Communications, 2006, pp. 696-699, vol. 259, Elsevier B.V.
Laser Optics, X-ray Toroids, Jun. 26, 2007, pp. 1-9.
International Search Report dated Jan. 5, 2012 in corresponding International Application No. PCT/IL2011/000675.

* cited by examiner

*Primary Examiner* — Courtney Thomas
(74) *Attorney, Agent, or Firm* — The Law Office of Michael E. Kondoudis

(57) ABSTRACT

An X-ray system is arranged for providing X-ray exposure to a target volume. The aforesaid X-ray system comprises an X-ray source and at least one focusing lens. The provided exposure is distributed over a volume of the target in a substantially uniform manner.

17 Claims, 12 Drawing Sheets

US 9,008,271 B2

SYSTEM FOR X-RAY IRRADIATION OF TARGET VOLUME

TECHNICAL FIELD

The present invention relates to an X-ray focusing system, and, more specifically, to an X-ray focusing system configured for therapeutic and surgical use.

BACKGROUND

Translation of X-rays from divergent sources into parallel beams and converging rays is subject to well-known limitations related to Bragg diffraction theory. Focusing optics for X-rays have been based on Johann or Johansson methods applied to curved single crystals. More recently, it has been shown that X-ray diffractors with doubly curved crystals can provide relatively greater throughput. The diffractor may be formed with a few pseudo-spherical curved dispersive elements. Even with these advances, formation of lens systems for X-ray optics has been limited by the size of practical crystal surfaces and the extent to which such surfaces can be configured to a desired curvature.

Presently, medical applications such as radiotherapy and radiosurgery use collimated X-rays for the destruction of malignant tissue. Radiotherapy is one of the major methods, sometimes the only method, in treating some types of cancer such as brain tumors. Linear accelerator systems generating X-rays have been widely used in radiotherapy in the destruction of such malignancies. Linear accelerator systems employed in radiotherapy, generally, use a multi-leaf collimator to create a shaped beam of X-rays. The shaped X-ray beam intensity has a flux density distribution which is identical along the beam path. The energy range of X-rays generated by such a system usually reaches MeV values to reduce surface or skin damage. To destroy a tumor, the linear accelerator system must be continually directed at, and rotated about the targeted malignant tissue. The high energy (MeV) of linear accelerator systems and their collimated rays expose a large amount of healthy tissue surrounding a tumor to a potentially damaging concentration of X-rays in the MeV range. Focused low-energy X-ray beam provides a high brightness focal spot which is used to treat a target in an accurate controlled fashion, as well as treat the target at an early stage. Lower energy X-rays have quicker fall-off behind the target and therefore reduce tissue damage to some sensitive organs which may be exposed to X-rays.

A system utilizing the X-ray focusing properties can achieve the same results with reduced damage to collateral tissue with an energy use in the 40-160 keV range. The advantages of using this focusing system include: reduced exposure and damage of healthy body tissue to X-rays, the X-rays in the 40 to 160 keV range can be focused directly at a malignancy with decreasing radiation intensity surrounding the X-ray focal point/treatment volume, eliminating damage to sensitive organs proximate the target.

U.S. Pat. No. 6,389,100 discloses a modular X-ray lens system for use in directing X-rays comprising a radiation source which generates X-rays and a lens system which forms the X-ray beam. The X-ray lens system is configured to focus X-rays to a focal point and vary the intensity of said focal point.

SUMMARY

It is hence one object of the invention to disclose an X-ray system arranged for providing X-ray exposure to a target volume comprising an X-ray source and at least one focusing lens. It is a core purpose of the invention to provide the exposure distributed over a volume of the target volume in a substantially uniform manner.

Another object of this disclosure is to disclose the above-mentioned invention wherein the X-ray source is substantially polychromatic.

A further object of this disclosure is to disclose the above-mentioned invention wherein the system comprises (a) an X-ray source; (b) at least one focusing lens configured for focusing radiation emitted by the source. The lens is axially symmetric. The lens comprises Bragg-type lens elements longitudinally arranged for Bragg X-ray diffraction of the radiation.

A further object of this disclosure is to disclose the above-mentioned invention, wherein lens elements are selected from the group consisting of a single crystal, a mosaic single crystal, HOPG (Highly Oriented Pyrolitic Graphite), a multilayer structure, a tiled single crystal element, and any combination thereof.

An emitting aperture of the source which is extendable such that the lens provides a substantially uniform convergent X-ray beam of a controllable waist size comparable with the dimensions of the target volume. Said aperture is of a variable shape.

A further object of this disclosure is to disclose the above-mentioned invention, wherein at least two lenses are arranged to provide converging X-rays to the target volume. The aforesaid lenses nested coaxially one into another are in the scope of the current invention.

A further object of this disclosure is to disclose the above-mentioned invention, wherein the lenses are coaxial. The lenses have different focal distances so that focal spots individually created by each lens element are longitudinally displaced to provide uniform X-ray exposure over the target volume.

A further object of this disclosure is to disclose the above-mentioned invention, wherein the X-ray system further comprises at least one lens segment having a symmetry axis which is angularly displaced relative to the symmetry axis, so that a focal spot created by the lens segment is transversely displaced relative to the focal spot created by at least one lens to provide laterally extended resultant focal spot with uniform X-ray exposure over the target volume.

A further object of this disclosure is to disclose the above-mentioned invention, wherein the X-ray system comprises changeable lenses configured with different focal distances and waist dimensions.

A further object of this disclosure is to disclose the above-mentioned invention, wherein the X-ray system is provided with a lens wheel being rotatable around an axis parallel to the lens axes. The lenses are changeable by means of rotation of the wheel.

A further object of this disclosure is to disclose the above-mentioned invention, wherein an X-ray focusing lens is configured for focusing radiation emitted by said source. The lens is axially symmetric; said lens comprising Bragg-type lens elements longitudinally arranged for Bragg X-ray diffraction of the radiation. A reflecting surface of the focusing lens is configured into a tiled structure. At least one tile of said structure has a convex surface of a predetermined negative radius, so that each of the tiles diffracts incident X-rays into a slightly divergent partial sub X-ray beam. The collection of all partial sub beams consists of an overall convergent total beam having divergence within convergence to form a converging lens with ordered artificial aberration.

A further object of this disclosure is to disclose the above-mentioned invention wherein a method of providing X-ray exposure to a target volume is disclosed. The method comprises the steps of: (a) providing a system arranged for providing X-ray exposure to a target volume; the system comprising (i) a substantially polychromatic X-ray source; (ii) at least one focusing lens configured for focusing radiation emitted by the source, the lens being axially symmetric; the lens comprising Bragg-type lens elements longitudinally arranged for Bragg X-ray diffraction of the radiation; (iii) emitting X-ray radiation; (b) focusing the emitted radiation by the focusing lens within the target volume. The radiation is emitted by an extendable aperture of variable shape of the source. The radiation is converted into a substantially uniform convergent X-ray beam in the target volume.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

The following description is provided, alongside all chapters of the present invention, so as to enable any person skilled in the art to make use of the aforesaid invention, and sets forth the best modes contemplated by the inventor of carrying out this invention. Various modifications, however, are adapted to remain apparent to those skilled in the art, since the generic principles of the present invention have been defined specifically to provide an X-ray system arranged for providing X-ray exposure to a target volume and a method of using the same.

Referring to the medical use of the X-ray system for tumor ablation, the known therapeutic devices comprising focusing elements are characterized by strong concentration of X-ray radiation in a sharp focal spot. It should be emphasized that uniform X-ray exposure of a target volume is a necessary condition of successful therapy or surgery because the optimal effect is achieved when all target tissue is exposed to a uniform dose. Thus, there is a long-felt and unmet need to provide a therapeutic device for X-ray ablation of tumors adapted for forming substantially uniform X-ray intensity within the target volume.

Figure 1:
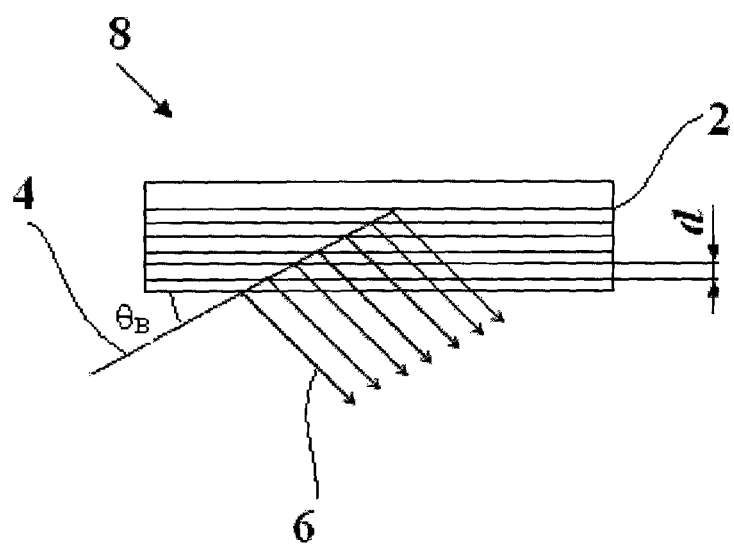
FIG. 1 is a schematic partial longitudinal cross sectional view of a crystal element (with schematic reflection planes) of an X-ray lens.

Reference is now made to FIG. 1, illustrating a simple Bragg reflector utilizing the principles of Bragg reflection. X-ray radiation 4 of wavelength λ is incident on a crystal having lattice planes 2 of plane spacing d. Narrow band or generally monochromatic radiation 6 is then reflected according to Bragg's Law. Bragg structures only reflect radiation when Bragg's equation is satisfied:

$$n\lambda = 2d \sin \theta_B, \quad (1)$$

where n is the reflection order, λ is the incident radiation wavelength, d is the lattice plane spacing, and $\theta_B$ is the Bragg angle.

Figure 2:
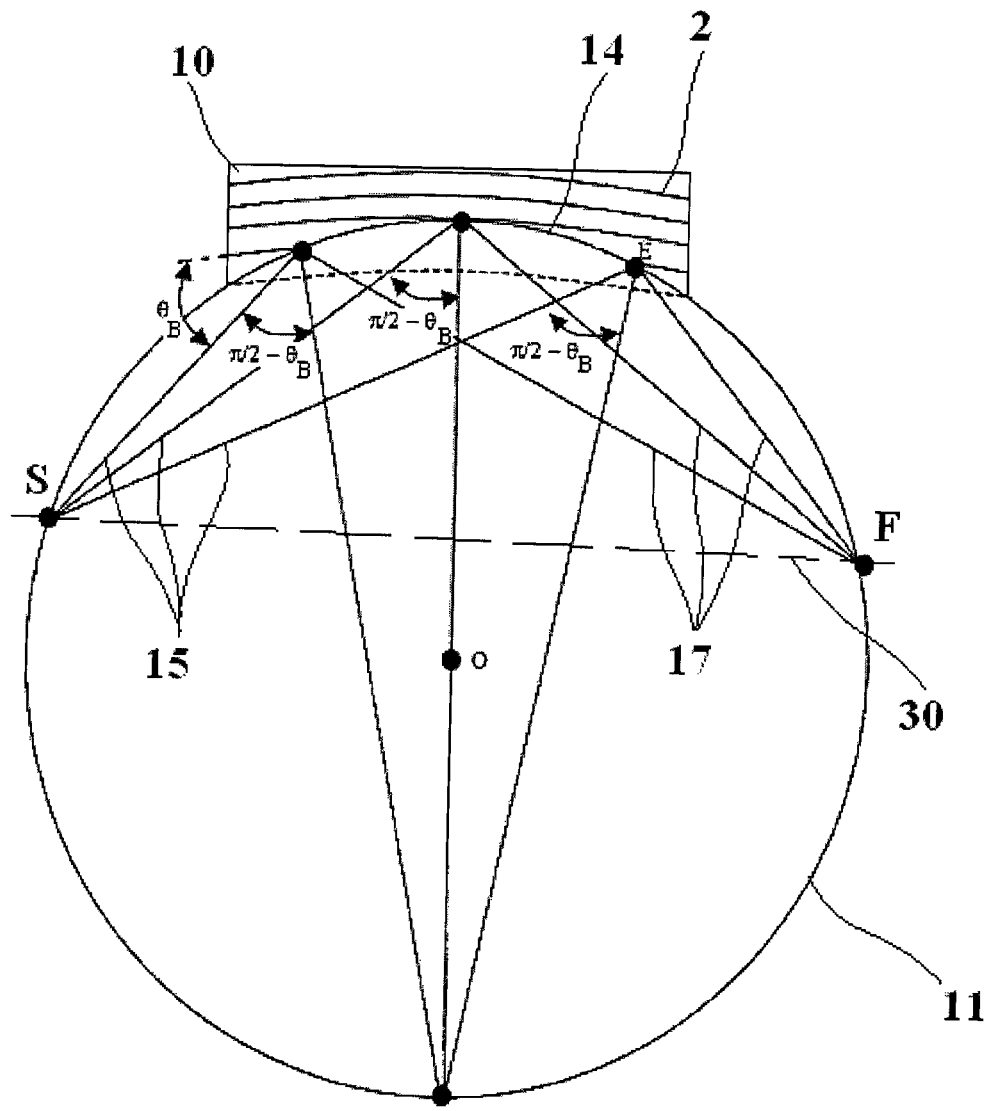
FIG. 2 is a two-dimensional diagram of the Johansson scheme.

Reference is now made to FIG. 2, presenting a 2D longitudinal cut of the Johansson scheme. A Johansson bent and machined crystal 10 is used to reflect and focus X-rays. The Johansson bent and machined crystal 10 reflects X-rays according to Bragg's law. The Johansson crystal 10 is made by bending a crystal into a barrel shaped surface with a longitudinal bending radius 2R, and then the reflection surface 14 is machined to a cylindrical surface with a longitudinal bending radius R. The angles of incidence of rays 15 generated by the X-ray source S and angles of reflection of rays 17 converging into the point F, are equal.

The transversal curvature radius of the machined surface at midpoint between the source and the focal point $r_s$ is given by:

$$r_s = L \tan \theta_B, \quad (2)$$

where L is a half of the distance from the radiation source to the focal point.

The Rowland radius R is given by the following expression:

$$R = \frac{r}{2\sin^2 \theta_B}. \quad (3)$$

Figure 3:
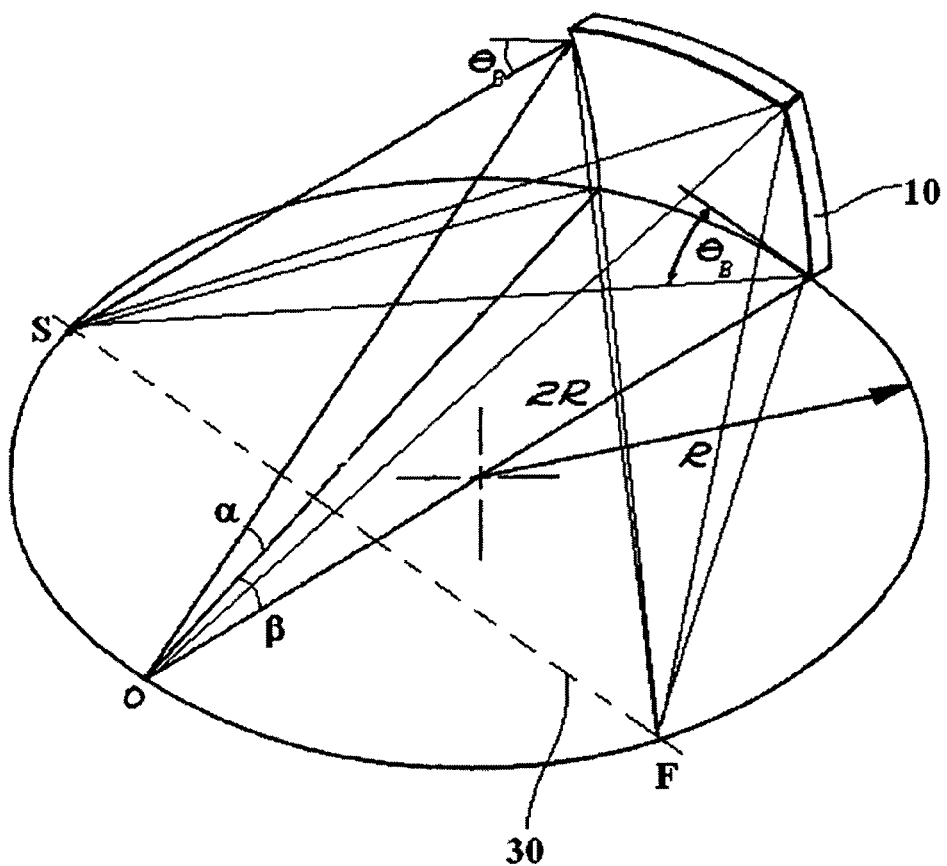
FIG. 3 is a three-dimensional diagram of the Johansson scheme.
Figure 4:
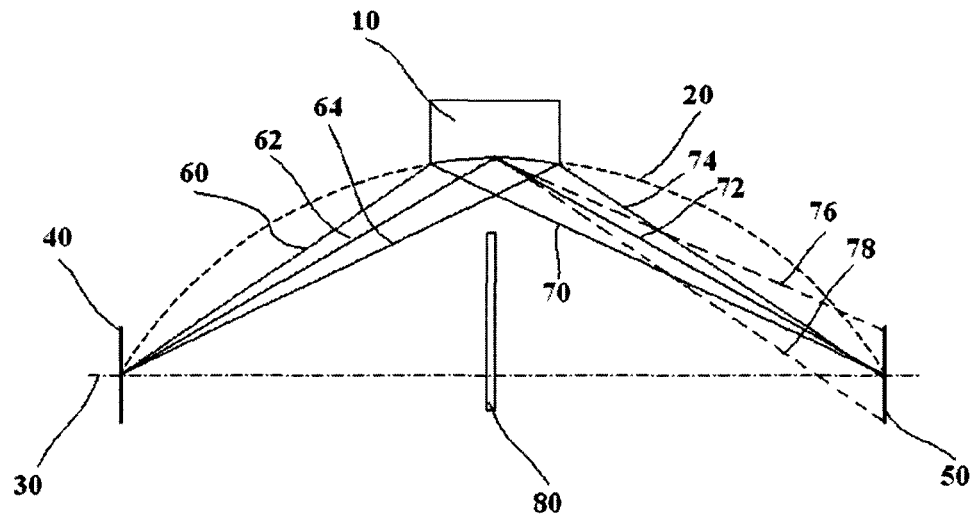
FIG. 4 is a schematic diagram of the X-ray focusing system provided with the substantially polychromatic X-ray source.

Reference is now made to FIG. 3, showing a 3D presentation of operation of the Johansson small bent crystal tile 10. As seen in FIG. 4, the crystal is bent in two directions. Specifically, an angle α lies in the saggital plane, while an angle β lies in the meridional plane.

The term "waist" hereinafter refers to a contour in a transversal cross section of the X-ray beam wherein beam intensity within the aforesaid contour does not fall below 50% of the peak intensity.

The term "uniform exposure" hereinafter refers to exposure transversal distribution of the X-ray beam within the waist which does not fall below 50% of the peak exposure.

The term "extendable aperture" hereinafter refers to an aperture placed in proximity of the X-ray source whose dimension may be varied between 0 and the X-ray emission spot of the X-ray tube.

The term "substantially polychromatic source" hereinafter refers to an X-ray tube of any anode material with any intensity distribution of emitted photon energies.

Reference is now made to FIG. 4, presenting an exemplary longitudinal half cross section of a system for X-ray exposure of the target volume. For simplicity, some elements disposed below the symmetry axis 30 are not shown. The system comprises an X-ray source constituting in an unlimited manner an X-ray tube with a tungsten anode and an X-ray reflecting lens. In accordance with Johansson geometry, X-rays 60, 62 and 64 outward from a center of an output aperture 40 of the X-ray source are reflected by a ring-like lens 10 into rays 70, 72 and 74, which are focused at a center of a focal plane 50. For example, the X-ray source emits substantially polychromatic radiation characterized by continuous energy spectrum with three peaks between 59 and 63 keV. An X-ray tube with a tungsten anode emitting spectral lines $K_{\alpha 1}$, $K_{\alpha 2}$ and $K_\beta$, is in the scope of the current invention. The lens 10 is configured to select the more intensive peak with energy 59.3 keV with a bandpass of approximately 3 keV. Rays 76 and 78 illustrate the influence of crystal mosaicity of the lens 10. The lens elements 10 are made sufficiently thick to stop most of the incident rays. In diffraction at inner crystalline planes, X-ray radiation of slightly different wavelengths is involved. The aforesaid phenomena result in broadening of the focal spot formed by the central ray 72.

Figure 5:
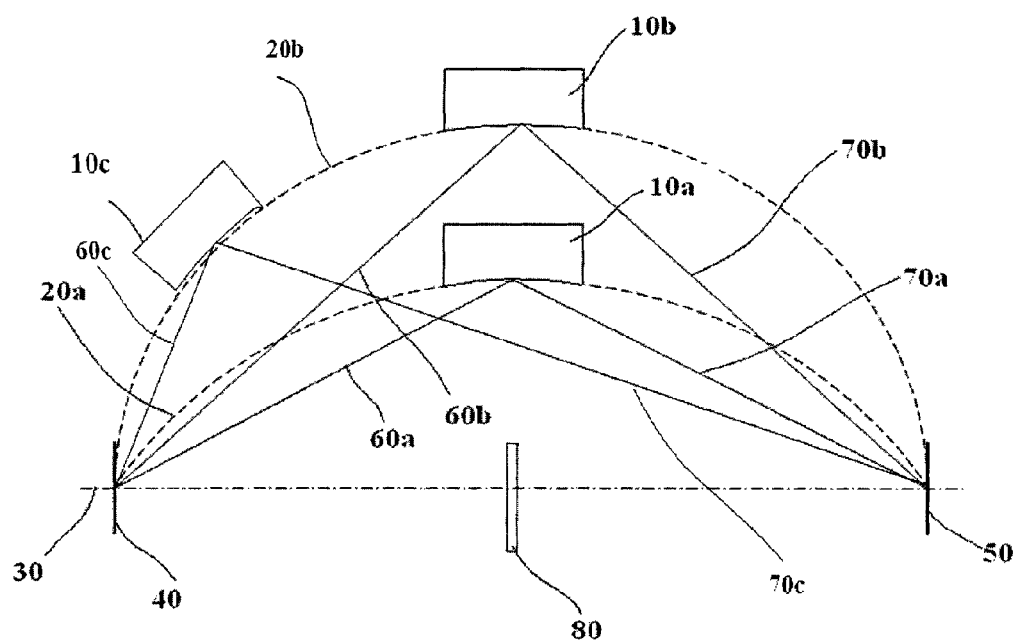
FIG. 5 is a schematic diagram of the X-ray focusing system provided with coaxially arranged lenses having the single focal spot.

Reference is now made to FIG. 5, presenting an exemplary longitudinal half cross section of a coaxially configured ring-like lens 10a, 10b and 10c having a common focal plane 50. The coaxial configuration allows for more portion of emitted X-ray radiation to be used for exposure of the target volume in the plane 50. As seen in FIG. 5, the lenses 10a and 10b belong to different Rowland circles 20a and 20b. Optionally, a lens 10c can be asymmetrically disposed on the Rowland circle 20b at different distances to the source 40 and the focal plane 50 and the rays 60c and 70c, respectively.

Figure 6:
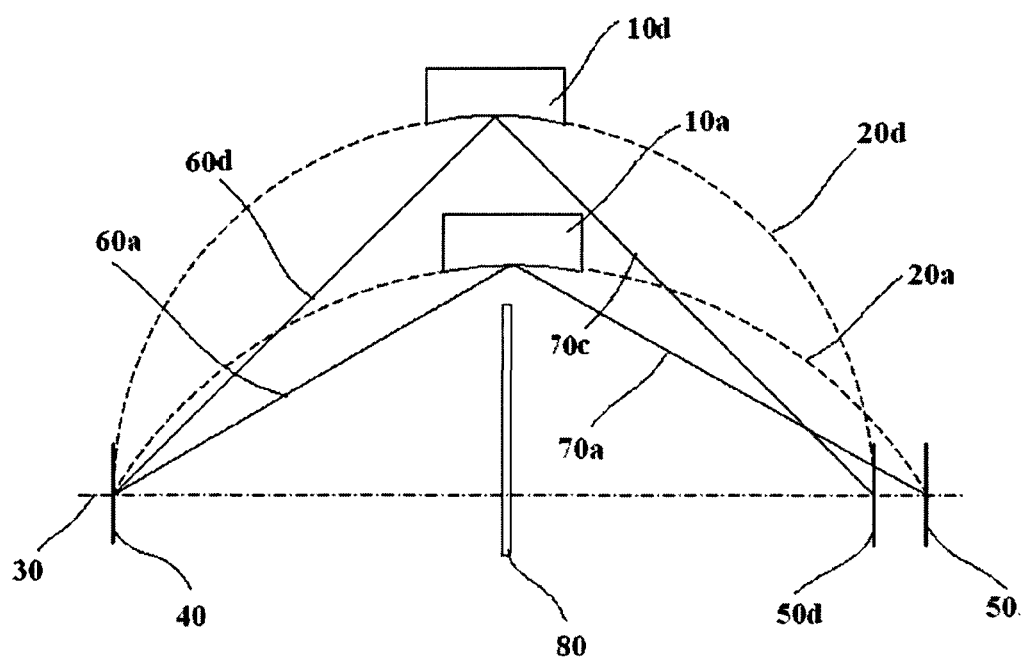
FIG. 6 is a schematic diagram of the X-ray focusing system provided with coaxially arranged lenses having the spaced-apart focal spots.

Reference is now made to FIG. 6, presenting an exemplary half cross section of coaxially configured ring-like lenses 10a and 10d, belonging to the different Rowland circles 20a and 20d, having longitudinally spaced-apart focal planes 50 and 50d, respectively. The aforesaid lenses 10a and 10d can be asymmetrically disposed similarly to lens 10c in FIG. 5. Longitudinal spacing of the focal planes 50 and 50d allows the exposure level over the target volume to be equalized.

Figure 7:
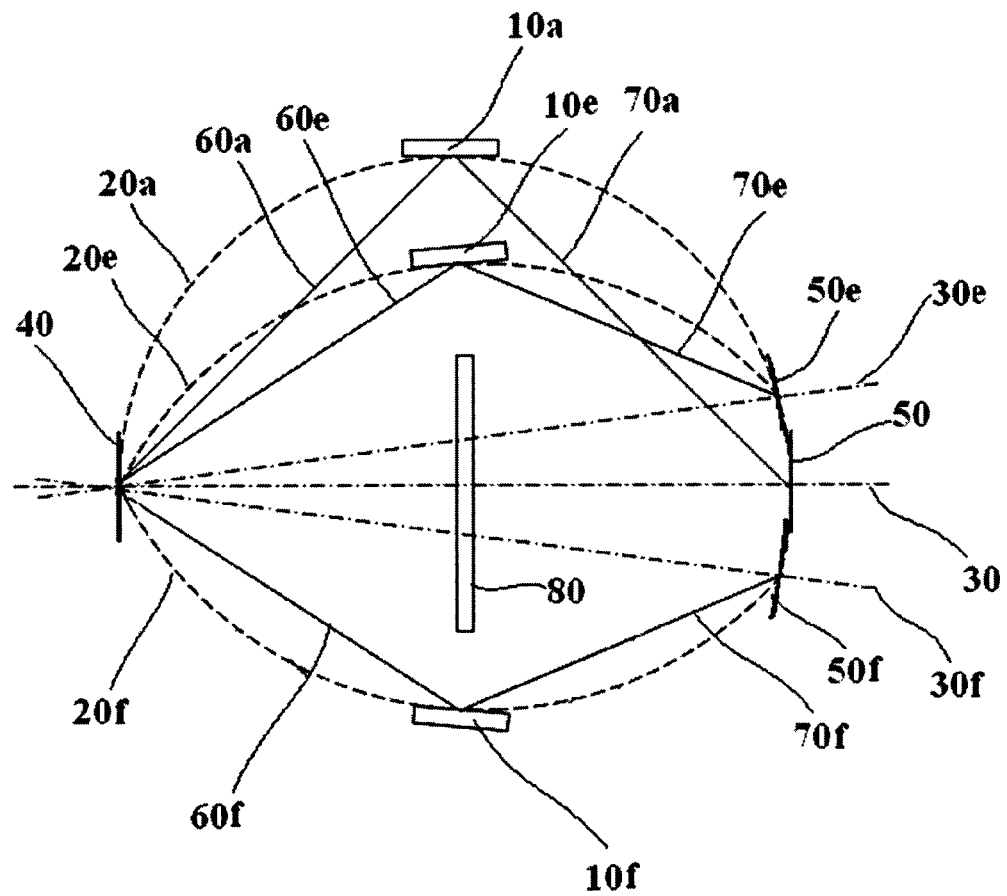
FIG. 7 is a schematic diagram of the X-ray focusing system provided with angularly displaced lens segments.

Reference is now made to FIG. 7, showing an embodiment of the current invention comprising at least one or more lenses arranged one inside each other 10a and at least two lens segments 10e and 10f belonging to different Rowland circles 20e and 20f having individual symmetry axes 30e and 30f, which are angularly displaced relative to the main lens axis 30. As seen in FIG. 7, the focal spots 50e and 50f created by the lens segments 10e and 10f, respectively, are laterally displaced relative to the main axis 30. The proposed technical solution provides improved lateral uniformity in the X-ray exposure of the target volume. The aforesaid lenses 10a, 10e and 10f can be asymmetrically disposed similarly to lens 10c in FIG. 5.

Figure 8:
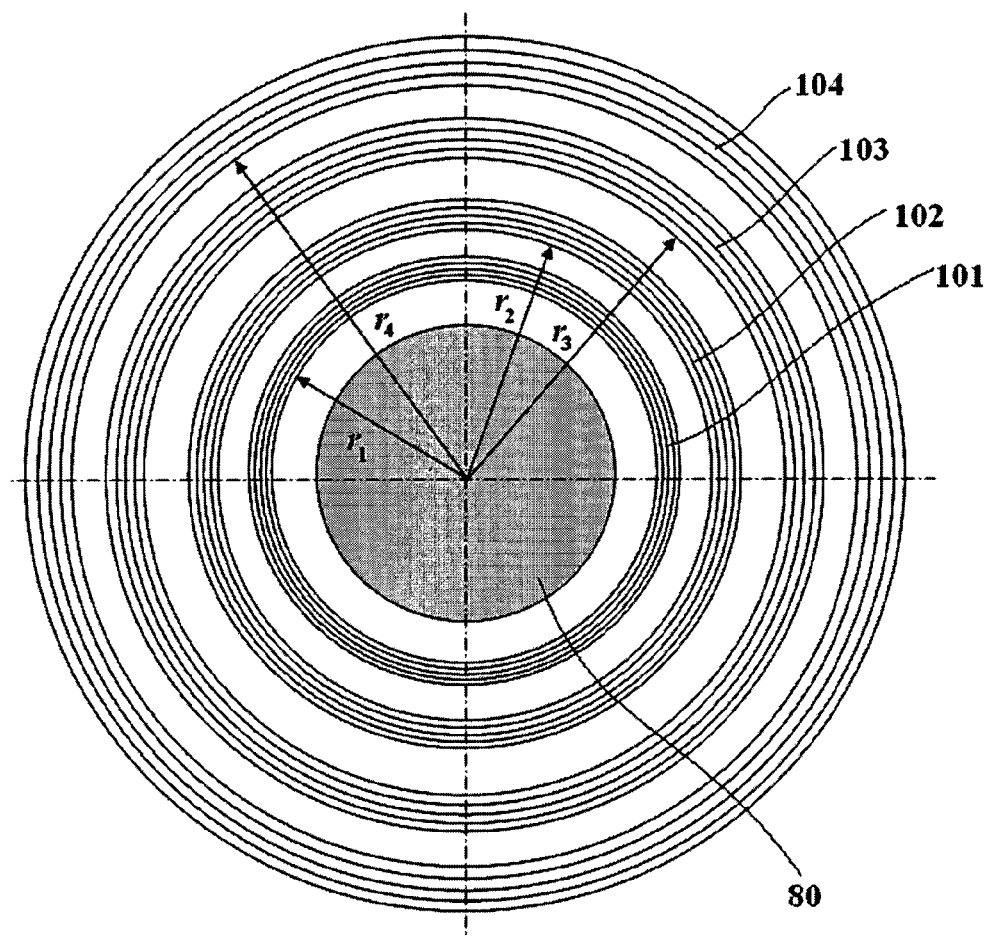
FIG. 8 is a lateral cross sectional view of the concentrically configured X-ray focusing system with schematic reflection planes.

Reference is now made to FIG. 8, presenting a lateral cross section of the concentrically configured lens system, which comprises ring-like lenses 101, 102, 103, and 104. The X-ray radiation propagating within the ring-like lens 101 is screened by the beam stop 80.

Figure 9:
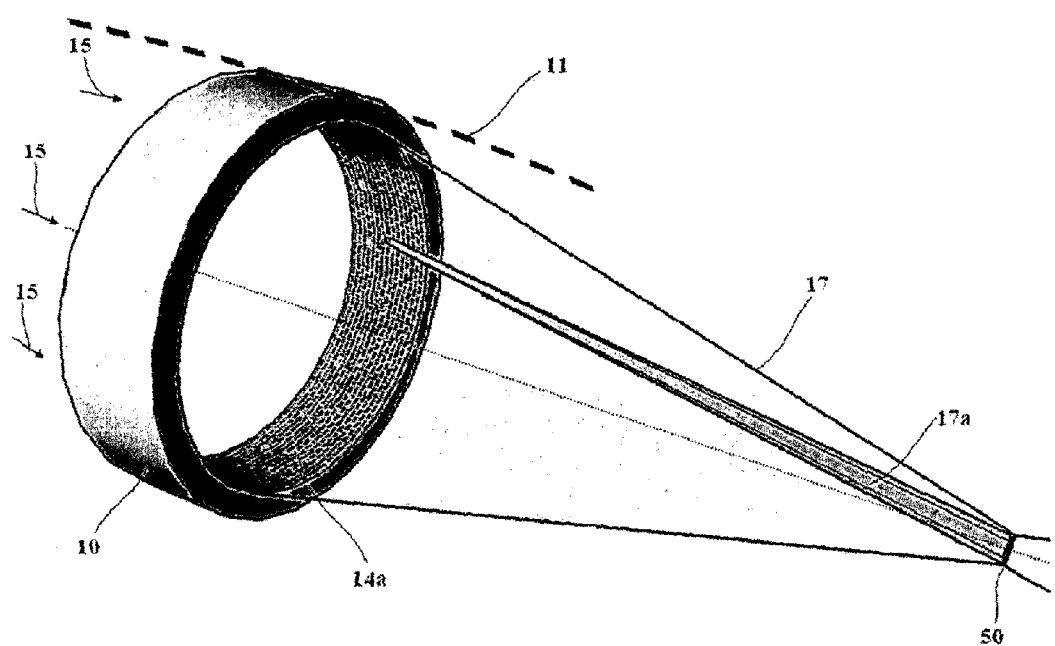
FIG. 9 is a three-dimensional schematic diagram of the X-ray tiled focusing system provided with slight angular diverging lens tiles arranged in an overall converging geometry establishing partial divergence within convergence; each small tile is machined as shown in FIG. 10.

Reference is now made to FIG. 9, presenting the ring-like lens 10. An internal reflecting surface is configured into a tiled structure 14a. At least one cell of the structure consists of a small crystal tile 14a exhibiting a convex surface of a predetermined negative radius. The incident X-rays 15 diffract into a converging total X-ray beam 17, consisting of a collection of slightly diverging sub X-ray beams 17a emerging from each tile. The beam 17a is an exemplary divergent beam diffracted on a single tile. The entire collection of slightly divergent beams from all tiles lies on an overall converging cone to a focal location with a finite waist 50.

Figure 10:
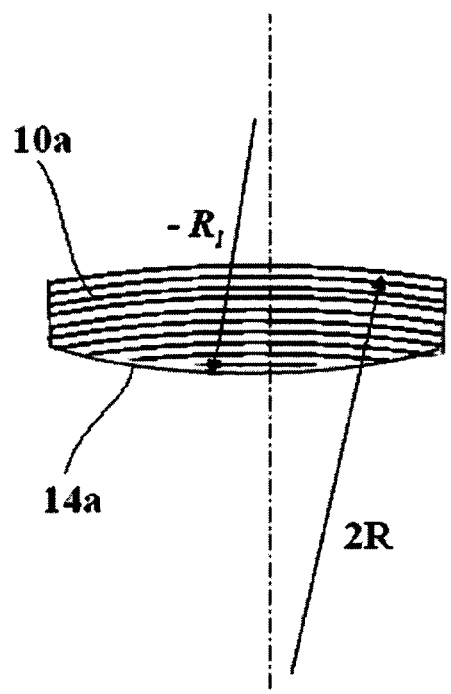
FIG. 10 is a schematic diagram of a single crystal tile of the tiled focusing system machined in a negative radius to allow for the slight divergence as a partial sub beam.

Reference is now made to FIG. 10, presenting meridional sections of the focusing lens 10 depicted in FIG. 9. FIG. 10 presents a profile of a single tile 10a. The operating surface 14a has curvature of the negative radius $-R_1$.

Figure 11:
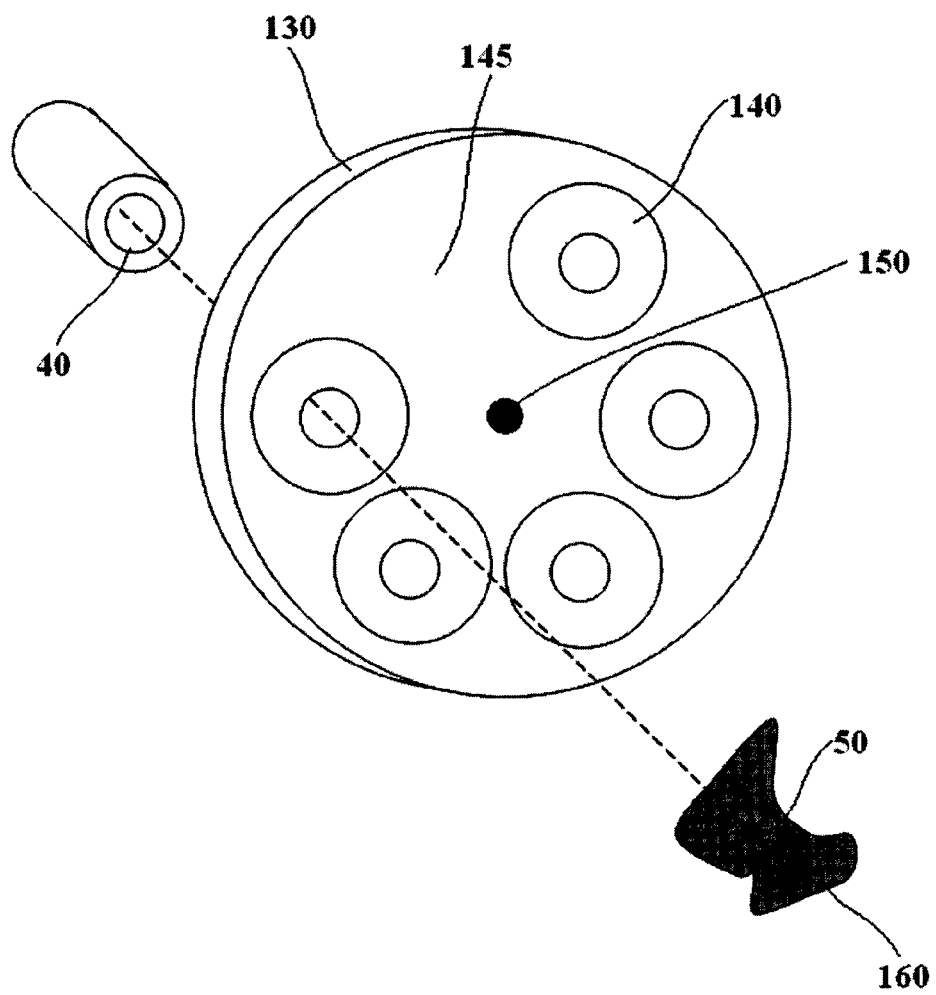
FIG. 11 is a schematic view of the X-ray focusing system provided with a lens wheel.

Reference is now made to FIG. 11, presenting an X-ray focusing system comprising an X-ray source with an output aperture 40 and a lens wheel 130. The aforesaid wheel 130 is rotatable around an axis 150. The wheel 130 is provided with a plurality of X-ray lenses 140. The aforesaid lenses 140 are characterized by different focal distances, and longitudinal and lateral dimensions of the focal area 50. A particular lens 140 is selected according to the characteristics of the tumor 160 to be treated. The depth and dimensions of the treatment area can be selected. The lenses 140 are changeable by means of rotation of said wheel 130. An area 145 screens the target volume 160 from the X-ray source 40 in the pauses between treatment sessions.

Figure 12:
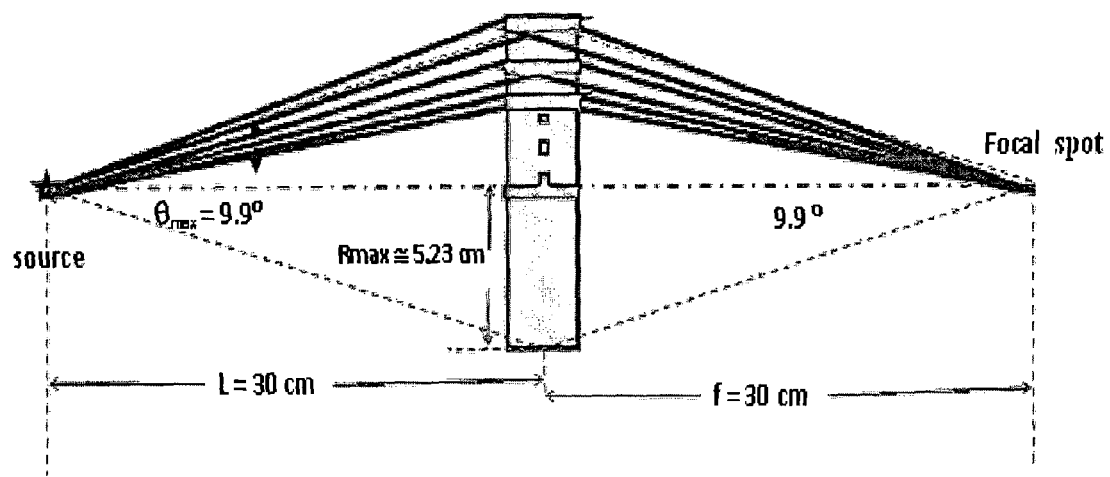
FIG. 12 is a schematic diagram of the exemplary lens system.

Reference is now made to FIG. 12, presenting a schematic diagram of an exemplary lens system comprising a number of reflecting X-ray lenses. Ring radii $r_s$ and Bragg angles $\theta_B$ are shown in Table 1 along with crystal plane distances d and Rowland radii R.

The formulae used in the calculations presented in Table 1 are Equations (2) and (3) above.

TABLE 1

| No. | Miller index | 2θ(deg) | d (Å) | r (cm) | R (cm) |
|---|---|---|---|---|---|
| 1 | 111 | 5.767 | 2.08712 | 1.51 | 298 |
| 2 | 200 | 6.661 | 1.8075 | 1.75 | 258 |
| 3 | 220 | 9.425 | 1.2781 | 2.47 | 183 |
| 4 | 311 | 11.056 | 1.089985 | 2.90 | 156 |
| 5 | 222 | 11.549 | 1.04356 | 3.03 | 150 |
| 6 | 400 | 13.344 | 0.90375 | 3.51 | 130 |
| 7 | 331 | 14.547 | 0.62934 | 3.82 | 120 |
| 8 | 420 | 14.927 | 0.80834 | 3.93 | 116 |
| 9 | 422 | 16.361 | 0.73791 | 4.31 | 106 |
| 10 | 333 | 17.361 | 0.69571 | 4.58 | 100 |
| 11 | 440 | 18.914 | 0.63905 | 5.00 | 92.5 |
| 12 | 531 | 19.789 | 0.61105 | 5.20 | 88.6 |

Considering mosaicity for the copper single crystal, a beam waist is generated at the focal plane given by $$w = \Delta\theta\sqrt{L^2 + r^2} \qquad (4).$$

For a realistic mosaicity of approximately 0.5°, the waist dimension w≅2.5 mm is calculated for all rings.

The invention claimed is:

1. An X-ray system arranged for providing X-ray exposure to a target volume; said system comprising
   (a) an X-ray source; and
   (b) at least one focusing lens configured for focusing radiation emitted by said source, said lens being axially symmetric; said lens comprising Bragg-type lens elements longitudinally arranged for Bragg X-ray diffraction of said radiation;
   wherein an emitting aperture of a variable shape of said source is extendable such that said lens provides a substantially uniform convergent X-ray beam of a controllable waist size comparable with dimensions of said target volume.

2. The X-ray system according to claim 1, wherein said X-ray source is substantially polychromatic.

3. The X-ray system according to claim 1, wherein at least two lenses are arranged to provide converging X-rays to the target volume.

4. The X-ray system according to claim 1, wherein at least two lenses coaxially nested one into another.

5. The X-ray system according to claim 3, wherein said lenses are coaxial; said lenses have different focal distances so that focal spots individually created by each lens are longitudinally displaced to provide substantially uniform X-ray exposure over said target volume.

6. The X-ray system according to claim 1, further comprising at least one lens segment having a symmetry axis which is angularly displaced relative to said symmetry axis so that a focal spot created by said lens segment is transversely displaced relative to said focal spot created by said at least one lens to provide laterally extended resultant focal spot with substantially uniform X-ray exposure over said target volume.

7. The X-ray system according to claim 4, 5 or 6, comprising changeable lenses configured with different focal distances and lateral and longitudinal dimensions of said focal spot.

8. The X-ray system according to claim 7, provided with a lens wheel being rotatable around an axis parallel to said lens axes; said lenses are changeable by means of rotation of said wheel.

9. An X-ray lens configured for focusing radiation emitted by said source, said lens being axially symmetric; said lens comprising Bragg-type lens elements longitudinally arranged for Bragg X-ray diffraction of said radiation; wherein a reflecting surface of said focusing lens configured into a tiled structure, at least one cell of said tiled structure has a convex surface of a predetermined negative radius, so that said cell diffracts incident X-rays into a diverging sub X-ray beam.

10. A method of providing X-ray exposure to a target volume; said method comprising the steps of:
    (a) providing a system arranged for providing X-ray exposure to a target volume; said system comprising:
        i. an X-ray source; and,
        ii. at least one focusing lens configured for focusing radiation emitted by said source, said lens being axially symmetric; said lens comprising crystal lens elements longitudinally arranged for Bragg X-ray diffraction of said radiation;
    (b) emitting X-ray radiation; and,
    (c) focusing said emitted radiation by said focusing lens within said target volume;
    wherein said radiation is emitted by an extendable aperture of a variable shape of said source; said radiation is converted into a substantially uniform convergent X-ray beam of a controllable waist size comparable with a size of said target volume.

11. The method according to claim 10, wherein said step of focusing is performed by at least two lenses arranged to provide converging X-rays to the target volume.

12. The method according to claim 10, wherein said step of focusing is performed by at least two lenses coaxially nested one into another.

13. The method according to claim 11, wherein said step of focusing is performed by said lenses which are coaxial; said lenses have different focal distances so that focal spots individually created by each lens are longitudinally displaced to provide uniform X-ray exposure over said target volume.

14. The method according to claim 10, wherein said step of focusing is performed by at least one lens segment having a symmetry axis which is angularly displaced relative to said symmetry axis so that a focal spot created by said lens segment is transversely displaced relative to said focal spot created by said at least one lens to provide extended resultant focal spot with laterally uniform X-ray exposure over said target volume.

15. The method according to claim 12, 13 or 14, comprising a step of replacing said lenses configured with different focal distances and waists.

16. The method according to claim 12, comprising a step of rotating a lens wheel around an axis parallel to said lens axes; said lenses are changeable by means of rotation of said wheel.

17. The method according claim 12, wherein said focusing is performed by a reflecting surface of said focusing lens configured into a tiled structure, at least one tile of said structure has a convex surface of a predetermined negative radius, so that said tile diffracts incident X-rays into a diverging partial sub X-ray beam within the overall converging beam.

* * * * *